United States Patent [19]
Vigdorchik et al.

[11] Patent Number: 5,248,304
[45] Date of Patent: Sep. 28, 1993

[54] SINGLE USE INTRAUTERINE INJECTOR

[76] Inventors: Michael Vigdorchik, 11938 Charter House La., St. Louis, Mo. 63146; Michael Glants, Itshak Sade 1466 Apt. 13, Afula Elite, Israel

[21] Appl. No.: 890,168

[22] Filed: May 29, 1992

[51] Int. Cl.⁵ .................................. A61M 31/00
[52] U.S. Cl. ................................ 604/278; 604/41
[58] Field of Search ............. 604/264, 278, 279, 275, 604/39, 43, 45, 41

[56]         References Cited
         U.S. PATENT DOCUMENTS

| | | | |
|---|---|---|---|
| 334,316 | 1/1886 | Ward et al. | 604/41 |
| 388,510 | 8/1888 | Terrell | 604/41 |
| 442,558 | 12/1890 | Trott | 604/41 |
| 526,353 | 9/1894 | Lamb et al. | 604/39 |
| 550,238 | 11/1893 | Allen, Jr. | 604/39 |
| 565,386 | 8/1896 | Meengs | |
| 805,826 | 11/1905 | Vidaver | 604/39 |
| 2,421,294 | 5/1947 | Shotton | 604/39 |
| 2,457,244 | 12/1948 | Lamson | 128/246 |
| 3,211,151 | 10/1965 | Foderick et al. | 604/278 |
| 3,394,705 | 7/1968 | Abramson | 604/278 |
| 3,848,602 | 11/1974 | Gutnick | 128/344 |
| 4,089,337 | 5/1978 | Kronner | 128/348 |
| 4,100,923 | 7/1978 | Southern | 128/348 |
| 4,335,719 | 6/1982 | Johnston | 604/41 |
| 4,664,114 | 5/1987 | Ghodsian | 128/344 |
| 4,775,362 | 10/1988 | Kronner | 604/96 |

Primary Examiner—Paul J. Hirsch
Attorney, Agent, or Firm—Grace J. Fishel

[57] ABSTRACT

A single use intrauterine injector for use in hysterosalpingography and other procedures requiring injection of a fluid into a uterus. The injector has an inflatable balloonlike member adjacent its tip for insertion into a cervical canal and by which the injector is held by fluid pressure against the walls of the cervical canal. A stop is provided on the injector for preventing insertion of the balloonlike member into the uterus.

10 Claims, 2 Drawing Sheets

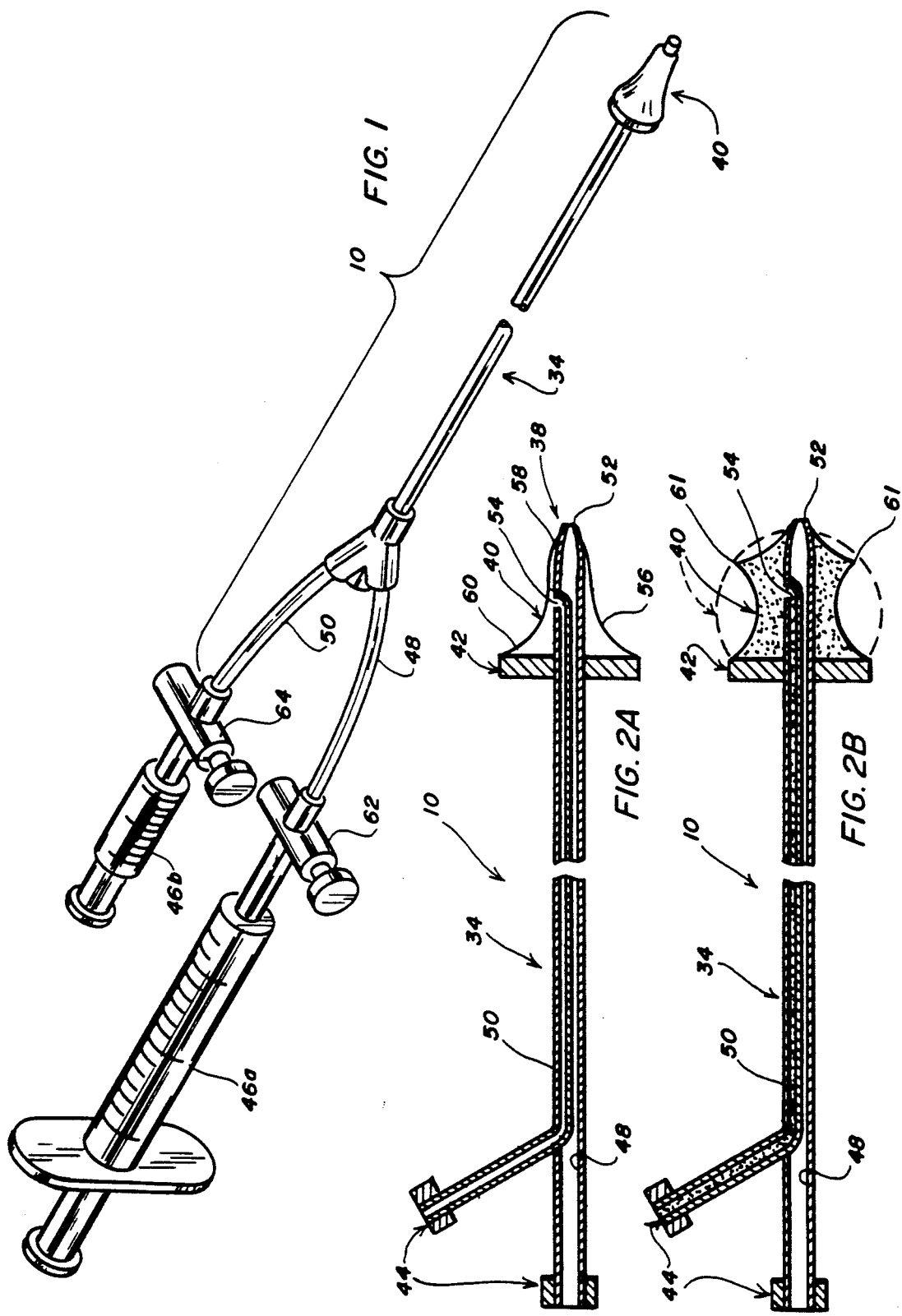

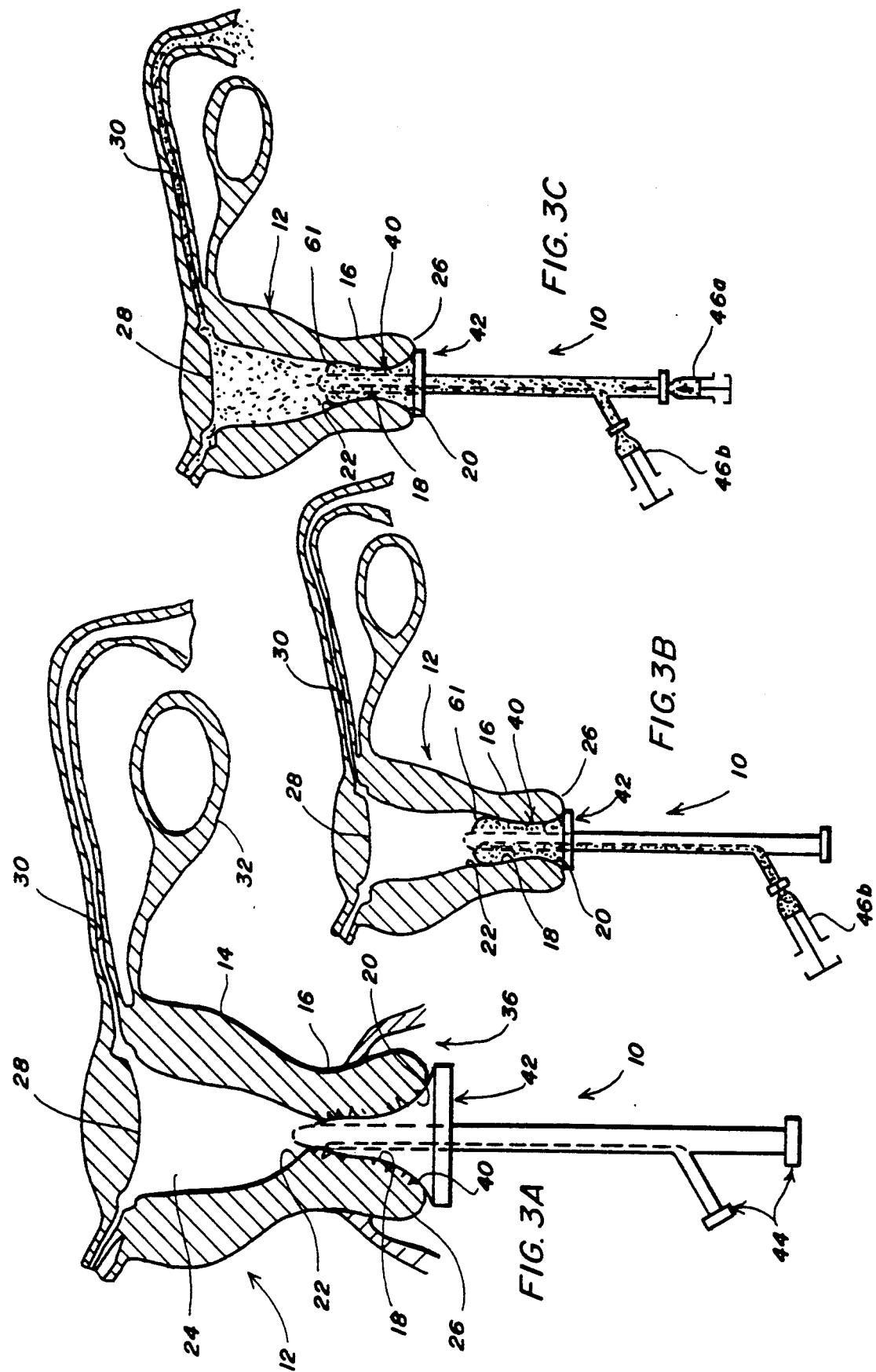

SINGLE USE INTRAUTERINE INJECTOR

The present invention relates to a disposable intrauterine injector with an inflatable balloonlike member adjacent its tip. The injector is held in a cervical canal by the balloonlike member without any other instruments. The subject single use intrauterine injector is for use in hysterosalpingography and the like.

BACKGROUND OF THE INVENTION

Healthy and open fallopian tubes facilitate conception and a normal intrauterine surface without polyps, submucous myomata, septa or scars allows the normal process of implantation to occur. An endocervical canal without diverticula, a lower segment without postoperative scars or defects and a normal internal cervical os may be important to a successful pregnancy.

Hysterosalpingography (HSG) is a radiologic examination for visualizing the above-mentioned areas and is useful in diagnosing the cause(s) of infertility. The procedure consists of taking fluoroscopic x-ray films as contrast medium flows through the uterus and the fallopian tubes. Normally, when a contrast material is placed into the uterus, it will flow freely through the fallopian tubes and into the peritoneal cavity. When there is a blockage in the tubes, flow of the contrast medium is stopped.

In addition to diagnosis, HSG has therapeutic value in patients with normal tubal patency as there is an increased rate of conception following HSG procedures. HSG is also used in assisted reproductive technologies for fertility enhancement to determine that the required conditions for success exist. For example, ovarian stimulation with intrauterine insemination requires the presence of at least one open fallopian tube for success. Gamete intrafallopian transfer and zygote intrafallopian transfer require that at least one tube be open and that it be of normal caliber. HSG is also indicated in patients who have previously undergone tubal cannulation procedures to document continued patency, since transfer attempts may induce damage or scarring in the tubal lumen.

Various intrauterine injectors for use in HSG have been designed. They require that the distance between the uterine fundus and the internal cervical os be determined. This is because the injectors extend well above the internal cervical os and the tip of the injector must be trimmed or adjusted so as to minimize the chance of perforating the uterus. In addition, when the tip of the injector is in the uterine cavity, the endocervical canal and the lower uterine segment may not be outlined with contrast in its entirety. Many of the injectors require the use of a tenaculum which is placed on the anterior cervical lip. A sufficient "bite" is essential because a single-tooth tenaculum may tear through the cervical tissue if a great deal of traction is applied. The tenaculum causes spotting and bleeding when removed and is associated with a cramp when it is applied. When a tenaculum is used, it is difficult to move the patient to obtain oblique radiographic views.

The ideal intrauterine injector for delivering x-ray contrast medium into the uterus should be easily installed and not require measuring the distance between the uterine fundus and the internal cervical os, avoid uterine and cervical trauma, provide maximum delineation of the uterine cavity, have no added discomfort due to instrumentation (e.g., not require a tenaculum), allow patient maneuverability for oblique films or the like and not require that medical personnel hold the injector in place. Ideally it should be for single use to avoid transmitted infection (e.g. AIDS) as a result of inadequately sterilized instruments. Various injectors have been proposed for HSG, none of which satisfy all of the above mentioned criteria.

OBJECTS AND SUMMARY OF THE INVENTION

It is an important object of the present invention to provide an intrauterine injector for use in HSG which satisfies the above-mentioned requirements for an ideal injector. Other objects and features of the invention will be in part apparent and in part pointed out.

In accordance with the invention, a single use intrauterine injector has a semi-rigid tubular member with an insertable end. An inflatable balloonlike member is positioned adjacent its insertable end. The balloonlike member is for insertion into a cervical canal. The tubular member also has a stop means adjacent its insertable end which allows insertion of the balloonlike member into the cervical canal but which prevents insertion into the uterus. The tubular member has first and second passageways. The first passageway forms a conduit through which fluid can be injected into the uterus. The second passageway is of somewhat lesser length than the first passageway and forms a conduit through which a fluid can be injected into the inflatable balloonlike member for inflating it. When the balloonlike member is inflated in the cervical canal, the injector is held by the fluid pressure exerted by the balloonlike member against the walls of the cervical canal.

Use of the injector does not require measurement of the distance between the uterine fundus and the internal cervical os and insertion of the injector does not cause uterine or cervical trauma. The entire uterine cavity can be visualized and there is no added instrumentation (such as a tenaculum) to cause patient discomfort, inhibit patient maneuverability or require medical personnel to hold.

The invention as summarized above comprises the constructions hereinafter described, the scope of the invention being indicated by the subjoined claims.

BRIEF DESCRIPTION OF THE DRAWINGS

In the accompanying drawings, in which one of various possible embodiments of the invention is illustrated, corresponding reference characters refer to corresponding parts throughout the several views of the drawings in which:

FIG. 1 is a perspective view of an intrauterine injector with an inflatable intracervical balloonlike member adjacent its tip in accordance with the present invention;

FIG. 2A is a side elevational view in section of the injector with the intracervical balloonlike member deflated;

FIG. 2B is a side elevation view in section of the injector with the intracervical balloonlike member inflated;

FIG. 3A is a sectional view illustrating intromitting the injector into the cervical canal;

FIG. 3B is a sectional view illustrating inflating the intracervical balloonlike member through a side tube; and, FIG. 3C is a sectional view illustrating injecting x-ray contrast medium into the uterine cavity through a central tube.

DETAILED DESCRIPTION OF THE INVENTION

Referring to the drawings more particularly by reference number, reference numeral 10 refers to an intrauterine injector in accordance with the present invention. Injector 10 is for use with a uterus 12 as illustrated in FIGS. 3A-3C. Uterus 12 is divided structurally and functionally into two parts, a body 14 and a cervix 16. Body 14 measures about 7.5 cm in length and cervix about 2.0 cm. A cervical canal 18 with an external cervical os 20 and an internal cervical os 22 communicates with a uterine cavity 24 within body 14. That end of cervix 16 toward the perineum protrudes into the cavity of the vagina as a free extremity 26. A fundus 28 is located opposite to internal cervical os 22 and a fallopian tube 30 (one on each side of fundus 28) conducts an ovum from an ovary 32 into uterine cavity 24.

As best seen in FIGS. 1 and 2A-2B, injector 10 is formed as a semi-rigid tubular member 34 for insertion through a vagina 36 into cervical canal 18 of a patient about to undergo HSG or the like. Tubular member 34 has an insertable end 38 and ma be made of a plastic material such as polyvinyl chloride or the like. An inflatable balloonlike member 40 and a stop means 42 are provided adjacent insertable end 38. Tubular member 34 is about 25 cm in length and an end opposite insertable end 38 (herein referred to as exterior end 44) is outside the vaginal opening. Joining exterior end 44 are a pair of syringes 46a, 46b, more particularly described hereinafter.

Tubular member 34 has a first passageway 48 and a second passageway 50. First passageway 48 runs the length of tubular member 34 and terminates at insertable end 38 with a rounded nose portion 52. Second passageway 50 is somewhat lesser in length than first passageway 48. That end of second passageway 50 adjacent insertable end 38 connects with a port 54 through which balloonlike member 40 is filled. First passageway 48 forms a conduit through which fluid can be injected into the uterus and second passageway 50 forms a conduit through which a fluid can be injected into the intracervical balloon for inflating same.

Stop means 42 encircles and is fixed to tubular member 34 adjacent insertable end 38 for abutment with free end 26 of cervix 16. Stop means 42 is illustrated as a disk and, like tubular member 34, is formed of a semi-rigid material such as polyvinyl chloride. Stop means 42 is sized so that it can be passed through the vaginal opening and brought into abutment against free end 26 of cervix 16. For this purpose, stop means 42 is made too large (e.g., about 30 mm in diameter) to pass through cervical canal 18. Stop means 42 is spaced from insertable end 38 a distance slightly greater than the length of cervical canal 18 such that insertable end 38 extends a short distance above internal cervical os 22. For this purpose, stop means 42 is spaced about 30 mm from the tip of insertable end 38.

Inflatable balloonlike member 40 is a sleeve 56 formed of a suitable thin film plastic material capable of being inflated to fully occupy and seal cervical canal 18. Sleeve 56 has a first end 58 and a second end 60. Sleeve 56 is sealingly engaged to tubular member 34 at first end 58 and sealingly engaged to stop means 42 at its second end 60. As shown in the drawings, inflatable balloonlike member 40 is adjacent but spaced a short distance (e.g., about 4 mm) from the tip of insertable end 38.

Syringe 46a is filled with a fluid to be injected into uterus 12 such as radiopaque material. Syringe 46a is attached to first passageway 48. A valve 62 may be provided for closing first passageway 48 to prevent fluid injected into the uterus from flowing back through the first passageway. Syringe 46b is filled with a fluid (such as air) to be injected into balloonlike member 40. A valve 64 may be provided for closing second passageway 50 to prevent deflating the balloonlike member.

Injector 10 may be packaged in a closed polyethylene sack and sterilized for single use to prevent transmission of infection. Injector 10 is for use in HSG and for other purposes where a fluid is to be injected into the uterus such as in assisted reproductive technologies. Details of its use in HSG follow.

HSG is a nonoperative procedure which can be performed on an outpatient basis. The procedure is scheduled before ovulation, usually between cycle day 5 and 11, to prevent the possible irradiation of a fertilized ovum. The patient is placed in a dorsolithotomy position and a speculum placed into the vagina for visualization of the cervix. Free end 26 of cervix 16 is cleaned and, as shown in FIG. 3A, insertable end 38 of tubular member 34 inserted until further passage is stopped by stop means 42. The speculum can then be removed.

Stop means 42 prevents balloonlike member 40 from being pushed into uterus 12 and the distance between insertable end 38 and stop means 42 also prevents the tip of tubular member 34 from advancing very far above internal cervical os 22. Mechanical complications, such as uterine perforation and so forth, are thereby avoided.

As shown in FIG. 3B, inflatable balloonlike member 40 is inflated (as illustrated in dotted lines) until injector 10 is held in cervical canal 18 by fluid pressure exerted by the balloonlike member against the walls of the cervical canal (as illustrated in full lines). Valve 64 is closed to prevent deflation. As shown in FIG. 3C, a fluid, such as x-ray contrast medium, is injected into uterine cavity 24 and valve 62 closed. The entire uterus can be visualized since only the tip of injector 10 protrudes a short distance above internal cervical os 22. No other instruments (like a tenaculum) are required because injector 10 is firmly held by balloonlike member 40 and, in consequence, the patient can be moved to obtain oblique radiographic views or walked to an x-ray room. Injector 10 is not uncomfortable and may be left in place as long as reasonably required and medical personnel may leave the room since they do not need to hold anything.

In view of the above, it will be seen that the several objects of the invention are achieved and other advantageous results attained. As various changes could be made in the above constructions without departing from the scope of the invention, it is intended that all matter contained in the above description or shown in the accompanying drawings shall be interpreted as illustrative and not in a limiting sense.

What is claimed:

1. A single use intrauterine injector for use in a patient having a vagina with a vaginal opening and a uterus with a cervical canal comprising a semi-rigid tubular member with an insertable end and an inflatable spool-shaped balloon member adjacent its insertable end for insertion into the cervical canal, said tubular member having a stop means that can be passed through the vaginal opening for abutment with an end of the cervical canal which allows insertion of the spool-shaped balloon member into the cervical canal but which prevents insertion of the spool-shaped balloon member into the uterus, said tubular member having first and second passageways, said first passageway forming a conduit through which fluid can be injected into the uterus and said second passageway being of somewhat lesser length than the first passageway and forming a conduit through which a fluid can be injected into the inflatable spool-shaped balloon member for inflating same whereby the intrauterine injector is held in the cervical canal by fluid pressure exerted by the spool-shaped balloon member against the walls of the cervical canal.

2. The intrauterine injector of claim 1 wherein the stop means is attached to the tubular member at a distance from the insertable end which is slightly more than the length of the cervical canal for an average patient.

3. The intrauterine injector of claim 1 wherein the stop means is about 30 mm from the insertable end.

4. The intrauterine injector of claim 1 wherein the first passageway includes a valve for closing the line to prevent fluid injected into the uterus from flowing back through the first passageway.

5. The intrauterine injector of claim 1 wherein the second passageway includes a valve for closing the line to prevent deflating the balloonlike member.

6. A single use intrauterine injector for use in a patient having a vagina with a vaginal opening and a uterus with a cervical canal comprising a semi-rigid tubular member with an insertable end and an inflatable sleeve for insertion into the cervical can adjacent the insertable end of the tubular member, said sleeve having first and second ends, said tubular member having a stop means that can be passed through the vaginal opening for abutment with an end of the cervical canal which allows insertion of the inflatable sleeve into the cervical canal but which prevents insertion of the inflatable sleeve into the uterus, said sleeve sealingly engaged with the tubular member at said first end and sealingly engaged with the stop means at said second end, said tubular member having first and second passageways, said first passageway forming a conduit through which fluid can be injected into the uterus and said second passageway being of somewhat lesser length than the first passageway and forming a conduit through which a fluid can be injected into the inflatable sleeve for inflating same whereby the intrauterine injector is held in the cervical canal by pressure exerted by the inflatable sleeve against the walls of the cervical canal.

7. The intrauterine injector of claim 6 wherein the stop means is a disc and the disc is attached to the tubular member at a distance from the insertable end which is slightly more than the length of the cervical canal for an average patient.

8. The intrauterine injector of claim 7 wherein the disc is about 30 mm from the insertable end and about 30 mm in diameter.

9. The intrauterine injector of claim 6 wherein the first passageway includes a valve for closing the line to prevent fluid injected into the uterus from flowing back through the first passageway.

10. The intrauterine injector of claim 6 wherein the second passageway includes a valve for closing the line to prevent deflating the balloonlike member.

* * * * *